United States Patent

Baird et al.

[11] Patent Number: 4,658,040
[45] Date of Patent: Apr. 14, 1987

[54] PROCESS FOR MANUFACTURING HETEROCYCLIC COMPOUNDS

[75] Inventors: David B. Baird; Ronald Baker; Brian R. Fishwick; Robert D. McClelland, all of Manchester, England

[73] Assignee: Imperial Chemical Industries PLC, London, England

[21] Appl. No.: 427,807

[22] Filed: Sep. 29, 1982

Related U.S. Application Data

[63] Continuation of Ser. No. 274,384, Jun. 17, 1981, abandoned, which is a continuation of Ser. No. 71,024, Aug. 29, 1979, abandoned, which is a continuation-in-part of Ser. No. 70,042, Aug. 27, 1979, abandoned, which is a continuation of Ser. No. 693,149, Jun. 7, 1976, abandoned, which is a continuation of Ser. No. 549,295, Feb. 12, 1975, abandoned, which is a continuation of Ser. No. 363,818, May 25, 1973, abandoned.

[30] Foreign Application Priority Data

Jun. 9, 1972 [GB] United Kingdom ............... 27005/72
Aug. 29, 1972 [GB] United Kingdom ............... 39948/72

[51] Int. Cl.⁴ .......................................... C07D 333/36
[52] U.S. Cl. ..................................................... 549/68
[58] Field of Search .......................................... 549/68

[56] References Cited

PUBLICATIONS

Hartough, Thiophene and Its Deriv., (1952) pp. 230, 231.
Rinkes Researches on Thiophen Deriv., (1932) pp. 1134–1142.
Steinkopf, J. Liebigs Ann. D. Chem., (1914) pp. 17–44.

Primary Examiner—Alan Siegel
Attorney, Agent, or Firm—Cushman, Darby & Cushman

[57] ABSTRACT

A process for the manufacture of the heterocyclic compounds of the formula:

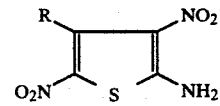

wherein R is hydrogen, lower alkyl or phenyl, which comprises simultaneously decarboxylating and dinitrating a compound of the formula:

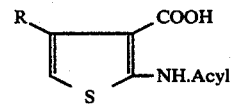

wherein R has the meaning stated above, and finally hydrolyzing off the acyl group.

1 Claim, No Drawings

PROCESS FOR MANUFACTURING HETEROCYCLIC COMPOUNDS

This is a continuation, filed June 17, 1981 now abandoned, which is a continuation of Ser. No. 71,024, filed Aug. 29, 1979, now abandoned, which is a continuation-in-part of Ser. No. 70,042, filed Aug. 27, 1979, now abandoned, which is a continuation of Ser. No. 693,149, filed June 7, 1976, now abandoned, which is a continuation of Ser. No. 549,295, filed Feb. 12, 1975, now abandoned, which is itself a continuation of Ser. No. 363,818, filed May 25, 1973, now abandoned.

This invention relates to a process for manufacturing heterocyclic compounds of the thiophene series.

According to the invention there is provided a process for the manufacture of the heterocyclic compounds of the formula:

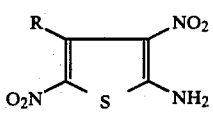

wherein R is hydrogen, lower alkyl or phenyl, which comprises decarboxylating and dinitrating a compound of the formula

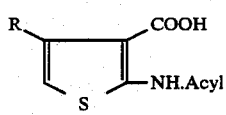

wherein R has the meaning stated above and finally hydrolysing off the acyl group, wherein the decarboxylation and dinitration are simultaneously carried out by contacting the compound of Formula I with a mixture of nitric and sulphuric acid, said nitric acid being present in amounts of at least 2 moles thereof per mole of the compound of Formula I at a temperature between $-20°$ and $30°$ C. and hydrolysing the acyl group of said decarboxylated and dinitrated compound by heating said compound with an aqueous or alcoholic solution of a mineral acid.

R is preferably lower alkyl and, above all, hydrogen.

As specific examples of the said acyl groups there may be mentioned formyl, acetyl, propionyl, benzoyl, methylsulphonyl, chloroacetyl, β-carboxypropionyl and p-toluenesulphonyl. It is however preferred that the acyl group is the residue —COX of a carboxylic acid X.COOH having a pK value not exceeding 4.3 and preferably not exceeding 3.8.

Examples of such carboxylic acids are formic (pK 3.75), chloroacetic (pK 2.85), succinic (pK 4.16) and phenylacetic (pK 4.28) acids.

The simultaneous dinitration and decarboxylation of the compound of Formula I can be carried out by stirring the compound in a mixture of nitric acid (at least 2 mols per mole of the compound of Formula I) and sulphuric acid which may contain free sulphur trioxide or up to 25% by weight of water, at a temperature between $-20°$ and $30°$ C.

The final hydrolysis of the acyl group can be effected by treating the dinitro compound with an aqueous or alcoholic solution of a mineral acid such as sulphuric acid preferably by heating to a temperature in the region of $100°$ C. It is not essential to isolate the dinitro compound prior to the hydrolysis since this can be effected by diluting the nitration mixture with the necessary amount of water, heating to hydrolyse off the acyl group and then isolating the resulting compound by conventional means; for example by further dilution with water, filtering off the solid which is precipitated. When the deacylation is carried out immediately after the nitration then it is preferred to add a substance such as sulphamic acid to destroy any nitrous acid or other oxidising agents present.

When R in the compound of Formula I represents a phenyl radical, then the conditions necessary for the dinitration of the thiophene nucleus may additionally introduce a nitro group or groups into the said radical. However, the production of such compounds also falls within the scope of the present invention.

The compounds of Formula I can themselves by obtained by treating a compound of the formula

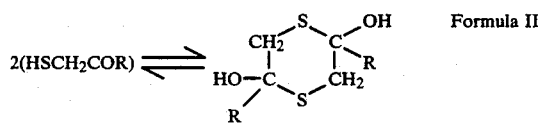

with cyanoacetic acid or an alkyl cyanoacetate such as ethyl cyanoacetate, or cyanoacetamide in aqueous alkaline medium optionally containing an aliphatic alcohol (for example an aqueous solution of sodium hydroxide) preferably at a temperature between $20°$ and $100°$ C. An acylating agent, for example acetic anhydride, is then added and the pH of the mixture is maintained between 4 and 10 preferably between 7 and 9 by the addition of alkali until the acylating is complete. If the acylating agent is an acid anhydride then control of the pH is not so essential provided that an excess of the anhydride is always present in the reaction mixture. The mixture is then acidified and the compound of Formula I which is precipitated is filtered off and dried.

As examples of acylating agents there may be mentioned acetyl chloride, chloroacetyl chloride, acetic anhydride, propionic anhydride, a mixture of formic acid and acetic anhydride, benzoyl chloride, p-toluene sulphonyl chloride, methane sulphonyl chloride, succinic anhydride and phthalic anhydride.

The compounds of Formula II can themselves be obtained by dimerisation of the corresponding mercaptoaldehyde or ketone of the formula HS.CH$_2$COR prepared for example by reaction of the appropriate haloaldehyde or haloketone with sodium hydrosulphide in aqueous medium. If desired the subsequent reaction with the cyanoacetic acid can be carried out without isolating the compounds of Formula II.

The heterocyclic compounds obtained by the process of the invention are valuable as diazo components in the manufacture of disperse monoazo dyestuffs.

The invention is illustrated but not limited by the following Examples in which the parts and percentages are by weight.

EXAMPLE 1

A mixture of 5.55 parts of 2-acetylaminothiophene-3-carboxylic acid and 27 parts of sulphuric acid monohydrate is stirred at $0°$ C. and a mixture of 10 parts of water, 30.4 parts of sulphuric acid and 7.0 parts of $80°$ Tw nitric acid is added dropwise, the temperature of the resulting mixture being maintained below $0°$ C. by external cooling. The mixture is then poured into a solution of 10 parts of sodium acetate in 250 parts of water, the temperature being maintained between 45° and 60° C. by the addition of ice, and the pH being maintained at 4 by the addition of a concentrated aqueous solution of sodium hydroxide. The mixture is stirred for 30 minutes at 50° C., then cooled to 25° C. and the precipitated 2-acetylamino-3:5-dinitrothiophene is filtered off, washed with water and dried. The yield is 2.6 parts (37.5%).

A mixture of 5 parts of 2-acetylamino-3:5-dinitrothiophene, 92 parts of sulphuric acid and 50 parts of water is stirred for 3 hours at 90° C. The mixture is then poured onto 150 parts of ice, and the precipitated 2-amino-3:5-dinitrothiophene is filtered off, washed with water and dried. The yield is 3.6 parts (88%).

The 2-acetylaminothiophene-3-carboxylic acid used in the above Example was itself obtained as follows:

46.5 Parts of cyanoacetic acid were added to a mixture of 50 parts of a 70° Tw aqueous solution of sodium hydroxide and 180 parts of water, followed by 38 parts of mercaptoacetaldehyde dimer. The resulting mixture was then heated for 5 minutes at 80° C. after which it was cooled to 20° C. 100 Parts of acetic anhydride were added during 15 minutes, the pH of the mixture being maintained between 6 and 7 by the addition of an aqueous solution of sodium hydroxide. The mixture was then filtered, the filtrates acidified with an aqueous solution of hydrochloric acid, and the precipitated solid filtered off, washed with water and dried. The product was obtained in a yield of 90%, and had a melting point of 216°–217° C.

EXAMPLE 2

11.1 Parts of 2-acetylaminothiophene-3-carboxylic acid are dissolved in 55 parts of sulphuric acid at 10°–20° C. The solution is cooled to 0° C., and 28 parts of a nitrating mixture (obtained by mixing together 633 parts of 20% oleum and 348 parts of nitric acid of sp.gr. 1.50) are gradually added whilst the temperature is maintained at −5° C. to 0° C. by external cooling. The mixture is stirred for 30 minutes, poured into ice and the precipitated 2-acetylamino-3:5-dinitrothiophene filtered off, washed with water, then with an aqueous solution of sodium acetate and dried. The N-acetyl group is then removed by heating in a hot aqueous solution of hydrochloric acid to give 2-amino-3:5-dinitrothiophene in an overall yield of 40%.

EXAMPLE 3

In place of the 11.1 parts of 2-acetylaminothiophene used in Example 2 there are used 11.9 parts of 2-acetylamino-4-methylthiophene-3-carboxylic acid whereby 2-amino-4-methyl-3:5-dinitrothiophene (m.pt. 157°–159° C.) is obtained.

The 2-acetylamino-4-methylthiophene-3-carboxylic acid was itself obtained as follows:

92.5 parts of chloroacetone were gradually added to 210 part of a 5M aqueous solution of sodium hydrosulphite, the temperature being maintained at 0° to 2° C. by external cooling. 120 parts of an aqueous solution of sodium hydroxide of sp.gr. 1.35 and 93 parts of cyanoacetic acid were then added, and the mixture stirred for 2 hours at 60° C. The mixture was filtered, cooled to 0°–10° C. and 200 parts of acetic anhydride added, the pH of the mixture being maintained between 7.5 and 9 by the simultaneous addition of sodium hydroxide, and the temperature being maintained between 5° and 10° C. The mixture was then filtered, the filtrate acidified with hydrochloric acid, and the precipitated 2-acetylamino-4-methylthiophene-3-carboxylic acid (m.pt. 234° C., yield 81%) was filtered off, washed with water and dried.

EXAMPLE 4

51.3 Parts of 2-formylaminothiophene-3-carboxylic acid are added to 500 parts of sulphuric acid (sp.gr. 1.84) at a temperature between 5° and 10° C., and 113.4 parts of a nitrating mixture (obtained by mixing together 633 parts of 20% oleum and 348 parts of nitric acid of sp.gr. 1.50) are then added at a temperature between −10° and −5° C. The mixture is then stirred for 1 hour at −5° C. to 0° C. and the mixture poured into 650 parts of ice and 250 parts of water containing 20 parts of sulphamic acid. The mixture is heated for 6 hours at 60° C., cooled and the precipitated 2-amino-3:5-dinitrothiophene filtered off, washed with water and dried.

EXAMPLE 5

In place of the 51.3 parts of 2-formylaminothiophene-3-carboxylic acid used in Example 4 there are used equivalent amounts of 2-(β-carboxypropionylamino)-thiophene-3-carboxylic acid or 2-(chloroacetylamino)-thiophene-3-carboxylic acid when 2-amino-3:5-dinitrothiophene is similarly obtained.

The 2-(β-carboxypropionylamino)thiophene-3-carboxylic acid was obtained as follows:

51.5 parts of an aqueous solution of sodium hydroxide of sp.gr. 1.35 was added, at a temperature below 20° C., to a solution of 26.4 parts of cyanoacetic acid in 102 parts of water, 21.5 parts of mercaptoacetaldehyde dimer were then added and the mixture stirred for 3 hours at 60°–70° C. The solution was then cooled to 5° C., 38 parts of succinic anhydride added at a temperature below 40° C., the pH of the mixture being maintained between 7.5 and 10 by the addition of sodium hydroxide. The pH was then adjusted to 7, the mixture filtered, the filtrate acidified and the solid (m.pt. 200°–202° C. (dec); yield 85%) filtered off, washed with water and dried.

The 2-(chloroacetylamino)thiophene-3-carboxylic acid was prepared in similar manner, the succinic anhydride being replaced by an equivalent amount of chloroacetyl chloride and the acylation being carried out at a temperature below 10° C.

EXAMPLE 6

5.55 parts of 2-acetylaminothiophene-3-carboxylic acid and a mixture of 20 parts of 20% oleum and 4 parts of nitric acid of sp.gr. 1.50 are simultaneously added to 30 parts of sulphuric acid monohydrate, the temperature of the mixture being maintained at −5° to 0° C. by external cooling. The mixture is then stirred for 1 hour at the same temperature, poured into a mixture of ice and water and the precipitated 2-acetylamino-3:5-dinitrothiophene filtered off, washed with water and dried. The product is then d-acetylated as previously described to give 2-amino-3:5-dinitrothiophene.

We claim:

1. A process for the manufacture of heterocyclic compound of the formula:

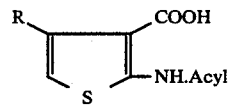

wherein R has the meaning stated above, and finally hydrolysing off and acyl group, wherein the decarboxylation and dinitration are simultaneously carried out by contacting said compound (a) with a mixture of nitric and sulphuric acid, said nitric acid being present in amounts of at least 2 moles thereof per mole of said compound (a) at a temperature between −20° and 30° C. and hydrolysing the acyl group of said decarboxylated and dinitrated compound by heating said compound with an aqueous or alcoholic solution of a mineral acid, the acyl group in the compound (a) being the residue —COX of a carboxylic acid X.COOH having a pK value not exceeding 3.8 whereby the yield of the said heterocyclic compound is 33% or more.

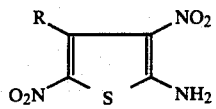

wherein R is hydrogen, lower alkyl or phenyl, comprising decarboxylating and dinitrating a compound (a) of the formula:

* * * * *